United States Patent [19]

Milbrath

[11] Patent Number: 5,401,634
[45] Date of Patent: Mar. 28, 1995

[54] STABLE BIOLOGICALLY ACTIVE FLUOROCHEMICAL EMULSIONS

[75] Inventor: Dean S. Milbrath, St. Paul, Minn.

[73] Assignee: Minnesota Mining and Manufacturing Company, Saint Paul, Minn.

[21] Appl. No.: 33,131

[22] Filed: Mar. 18, 1993

Related U.S. Application Data

[63] Continuation of Ser. No. 962,497, Oct. 16, 1992, abandoned, which is a continuation of Ser. No. 434,586, Nov. 13, 1989, abandoned, which is a continuation of Ser. No. 894,010, Aug. 7, 1986, abandoned.

[51] Int. Cl.⁶ .............. C12Q 1/68; G01N 33/53; G01N 33/543; G01N 33/544
[52] U.S. Cl. .................. 435/6; 435/7.1; 436/518; 436/528; 436/804; 264/4.1; 428/402.2; 210/656
[58] Field of Search .............. 435/6, 7.1; 436/518, 436/528, 804; 264/4.1; 428/402.2; 210/656

[56] References Cited

U.S. PATENT DOCUMENTS

| | | | |
|---|---|---|---|
| 3,806,417 | 4/1974 | Beaucamp et al. | 195/63 |
| 3,843,443 | 10/1974 | Fishman | 195/63 |
| 3,969,287 | 7/1976 | Jaworek et al. | 260/8 |
| 4,252,827 | 2/1981 | Yokoyama et al. | 424/366 |
| 4,267,273 | 5/1981 | Smith | 435/44 |
| 4,397,870 | 8/1983 | Sloviter | 424/325 |
| 4,423,077 | 12/1983 | Sloviter | 424/325 |
| 4,514,500 | 4/1985 | Giaever et al. | 435/241 |
| 4,619,897 | 10/1986 | Hato et al. | 435/182 |
| 4,619,904 | 10/1986 | Giaever et al. | 436/518 |
| 4,634,681 | 1/1987 | Giaever et al. | 436/518 |

FOREIGN PATENT DOCUMENTS

| | | | |
|---|---|---|---|
| 0222341 | 5/1982 | European Pat. Off. | |
| 0100660 | 2/1984 | European Pat. Off. | |
| 0200486 | 11/1986 | European Pat. Off. | |
| 2079936A | 1/1982 | United Kingdom | G01N 33/54 |
| 2079937A | 1/1982 | United Kingdom | G01N 33/54 |
| WO85/00664 | 2/1985 | WIPO | |

OTHER PUBLICATIONS

Obraztsov et al., "Binding of Proteins and Phospholipids by Emulsion of Perfluoroorganic Compounds", Institut of Biological Physics of the Academy of Sciences of USSR, Pushchino (1984).
Keese et al., "Cell Growth on Liquid Interfaces: Role of Surface Active Compounds", *Proc. Natl. Acad. Sci.*, vol. 80, pp. 5622–5626 (1983).
Robert P. Geyer, "The Design of Artificial Blood Substitutes", *Drug Design*, vol. VII, pp. 1–58.
Robert P. Geyer, "Whole Animal Perfusion with Fluorocarbon Dispersions", *Federation Proceedings*, vol. 29, 1970, pp. 1758–1763.
Merck Index, 10th Ed., p. 1090 (1983).
"Immobilization of Enzymes on Polytetrafluoroethylene Particles Packed in HPLC Columns", *Biotechnology and Bioengineering*, vol. XXIII, pp. 1913–1917 (1981).
Kensal Edward Van Holde, *Physical Biochemistry*, "Sedimentation", pp. 98–121, Viscosity, pp. 141–157, Prentice-Hall, Inc. Englewood Cliffs, N.J. (1971).
"Diuretics to Emulsions", *Encyclopedia of Chemical Technology*, 3rd Ed., vol. 8, pp. 900–901 (1979).
Sloviter et al., "Erythrocyte Substitute for Perfusion of Brain", *Nature*, vol. 216 (1967) pp. 458–460.
NEN Research Product Cat. of 1988, p. 168.

*Primary Examiner*—Mindy B. Fleisher
*Attorney, Agent, or Firm*—Gary L. Griswold; Walter N. Kirn; Paul W. Busse

[57] ABSTRACT

Fluorochemical emulsions comprised of a fluorochemical droplet discontinuous phase and aqueous continuous phase with at least one specific binding species immobilized on the fluorochemical droplets are shown. The emulsions may include a primer material to couple to specific binding species to the fluorochemical droplets. The emulsions may be used in diagnostic procedures or biochemical reactors where binding of the immobilized specific binding species to its binding partner is desired. The droplets may also incorporate a species which is detectable by spectrophotometric, fluorometric or colormetric means or a precursor to a detectable species.

23 Claims, No Drawings

STABLE BIOLOGICALLY ACTIVE FLUOROCHEMICAL EMULSIONS

This application is a continuation of U.S. application Ser. No. 07/962,497, filed Oct. 16, 1992, abandoned, which is a continuation of U.S. application Ser. No. 07/434,586, filed Nov. 13, 1989, abandoned, which is a continuation of U.S. application Ser. No. 894,010, filed Aug. 7, 1986, abandoned.

FIELD OF THE INVENTION

The present invention relates to fluorochemical emulsions which carry on the droplet surface one member of a specific binding pair. The novel emulsions of this invention are useful as diagnostic supports and as supports for biochemical reactions.

BACKGROUND OF THE INVENTION

Supports for antigen/antibody assays and biochemical reactions are typically latex beads, paper, fixed red blood cells and insoluble polymers such as dextran and polystyrene. In these assays and biochemical reactions at least one member of a specific binding pair (hereinafter a "specific binding species") is immobilized on a support and thereafter subjected to chemical reactions, physical manipulation or both in a manner that ultimately results in its binding (transitory or permanent) of the other member of the specific binding pair to the specific binding species. This coupling of the two members of the specific binding pair is useful to detect qualitatively or quantitatively the presence of one of the species in a sample as in a competitive assay, an immunoassay, a protein binding assay. Similarly, the binding of the two members of the specific binding pair can be used to take advantage of the inherent properties of one of the species, e.g., an enzymatic property.

A persistent problem in designing assays and reaction. Systems is the difficulty in immobilizing the specific binding species on the support so that it will withstand washings and remain on the support under the contemplated chemical conditions. Another problem is denaturing the specific binding species pair, i.e., reversing prematurely the binding of the two species such that the bound member disassociates from the immobilized member or the immobilized member and the bound member disassociate from the support. Reactivity of the support under the contemplated conditions of use, resulting in nonspecific binding of constituents in a test sample, is another persistent problem.

Microcapsules have been suggested for use as supports in immune response assays. UK patent Application 2,079,937 A (published 27 Jan. 1982) and UK patent Application 2,079,936 A (published 27 Jan. 1982) both describe making microcapsules with crosslinked wall materials encapsulating an oily core substance. Functional groups with sites for binding an antigen or antibody are attached to the wall by a crosslinking agent.

Fluorocarbon emulsions have been suggested for use as in vivo erythrocyte substitutes. Some fluorocarbon emulsions seem to have good oxygen transport characteristics and appear to be nontoxic and safely metabolized. Other fluorochemical emulsions have been shown to be toxic in laboratory animals or not metabolized and eliminated. Geyer describes various emulsions in Chapter 1, "The Design of Artificial Blood Substitutes", *Drug Design*, Vol. VII Academic Press, N.Y. (1976) and in "Whole Animal Perfusion with Fluorocarbon Dispensors" Federation Proceedings, Vol. 29 No. 5, p. 1758, (1970). Serum albumin, phospholipids (including lecithin), and surfactants such as Pluronic-F68 (Wyandotte Chemical Corp., Wyandotte, Mich.) have been used as emulsifying agents.

For use as artificial blood Sloviter in U.S. Pat. No. 4,423,007, has suggested emulsions of perfluoro compounds coated with a non-antigenic lipid, preferably egg yolk phospholipid or lecithin, in aqueous medium. He reports In U.S. Pat. No. 4,397,870 that the duration of effective droplet levels in the bloodstream is brief owing to the apparent removal of the lecithin coating and exposure of the perfluoro droplet surface in the bloodstream. Infusion of the patient who has previously received an infusion of an emulsion of coated droplets with the same substance used to coat the perfluoro compound droplet is recommended.

Sloviter in "Erythrocyte Substitute for Perfusion of Brain" *Nature Vol.* 216, Nov. 1967, 458, has also suggested dispersing a perfluoro compound in a simulated blood plasma compound of 8% bovine serum albumin in Krebs Ringer bicarbonate buffer. After the emulsion was formed and sedimented all soluble protein was washed away. The sedimented material was analyzed and found to contain about 5% protein.

The Japanese have also been active in the field of artificial blood. U.S. Pat. No. 4,252,827 is directed to fluorocarbon compound emulsions that are sufficiently stable to be kept for a long period of time without change in droplet size and can be mixed with plasma extenders such as dextran and hydroxyethyl starch. It describes an emulsion in an organic medium having a perfluorocarbon compound with 9 to 11 carbon atoms, a perfluoro-tert-amine having 9 to 11 carbon atoms, a surfactant having a molecular weight of about 2,000 to 20,000, a phospholipid and at least one fatty acid.

The effect of perfluoro organic compound emulsions on serum proteins and phosolipids has been studied by V. V. Obraztsuv et al. "Binding of Proteins and Phospholipid by Emulsion of Perfluoro Organic Compounds" *Ftoruglerodrye Gazoperrnosyaschchie Sridy* [531 FA5] 1984 147–52 (Russ). The protocol followed by these authors is not clear. They appear to have analyzed the amount of protein and phospholipids removed from solution only at equilibrium conditions. They do not report any experiments attempting to wash adsorbed protein and phospholipid off the emulsion droplets. They state "irreversible and denaturant character of binding of proteins by the hydrophobic surface raises the question to what extent the concentration of the proteins in the blood might be decreased as a result of the extensive blood substitution with PFOC emulsion."

SUMMARY OF THE INVENTION

The present invention is a stable emulsion having an aqueous continuous phase and a fluorochemical droplet discontinuous phase. At least one specific binding species is immobilized at the surface of the fluorochemical droplets without loss of specific binding capability. As used herein the term "specific binding species" refers to one member of a specific binding pair. The emulsions of the present invention are easily prepared and surprisingly stable over long periods of time. The emulsions withstand washings without loss of specific binding capability.

The relative inertness of fluorochemical to biological molecules as compared to conventional supports makes them ideally suited for use in a wide variety of circumstances. Representative examples of specific binding species which can be immobilized on fluorochemical droplets include one member of an antigen/antibody pairs where the antigen is a naturally occurring or synthetic protein, peptide, polysaccharide, lipid, nucleic acid, organic polymer, an antigenic fragment of these materials, an infectious agent such as bacteria or virus or a portion of their cell surface, a hapten such as a drug, hormone, or organic molecule and combinations and derivatives thereof; a molecule or segment of naturally occuring or synthetic DNA or RNA; an enzyme such as alkaline phosphatase, peroxidase, or beta-galactosidase, luciferass, urease, or other enzymes selected from oxidoreductases, transfereases, hydrolyases, kinases or lyases; another reaction catalyst; a lectin; a sugar; a cell surface marker or receptor; and a therapeutic substance such as a drug, plant extract, hormone or metabolites of these; the other member of the specific binding pair for each of the foregoing; and other components of specific binding reaction schemes such as dyes, fluorescent molecules, or components which in specific binding reaction schemes can be used to produce color, fluorescence, phosphorescence, chemiluminescence or other detectable products.

Another aspect of the invention involves immobilization of combinations of different specific binding species on tile same emulsion droplets. Emulsions having a combination of specific binding species and other components of their specific binding reaction scheme are particularly useful in diagnostic systems. Thus one member of an antigen/antibody binding pair and a material which is or reacts to form a detectable product such as an enzyme, dye, fluoroescent molecule, or chemiluminescent reagent can be independently immobilized on emulsion droplets. Immobilization of multiple specific binding species allows the immobilization of the separate components of an enzyme cascade which can be used to determine the presence and amount of a substance. For example glucose can be detected with the enzymes glucose oxidase and peroxidase linked to the same emulsion droplet.

The specific binding species may be immobilized on the fluorochemical droplet by direct adsorption at the droplet/aqueous interface. Alternatively a primer material may be used. A "primer material" is a material which has the ability to couple a specific binding species to a fluorochemical droplet. Naturally occurring or synthetic polymers with amine, carboxyl, mercapto, or other functional groups capable of specific reaction with coupling agents and highly charged polymers are preferred. The specific binding species may be immobilized by covalently bonding it to a primer material and adsorbing the conjugate at the interface of the discontinuous and the continuous phases. Alternatively the specific binding species may be adsorbed to a primer material and the resulting complex adsorbed at the interface of the continuous and discontinuous phases. The same result can be achieved by forming an emulsion with an aqueous continuous phase and a fluorochemical discontinuous phase using a primer material as an emulsifying agent. Then the biologically aetive moiety may be adsorbed or conjugated to the primer material at the interface of the continuous and discontinuous phases.

Yet another aspect of the invention involves incorporating a "dye" into the fluorochemical droplet. "Dyes" as used herein are species which can be detected by spectrophotometric, fluorometric or colorimetric means.

The process of the present invention involves providing an in vitro emulsion having an aqueous continuous phase and a fluorochemical discontinuous phase. At least one specific binding species is immobilized on the fluorochemical droplets. The fluorochemical droplets and immobilized specific binding species are contacted with an aqueous solution containing the specific binding partner of the specific binding species for a period of time sufficient to permit binding of the specific binding species to its partner. The process is preferably used in diagnostic procedures such as agglutination assays, sandwich or reverse inhibition enzyme immunoassays or radio immunoassays, or a protein binding assay.

DETAILED DESCRIPTION

The emulsions of the present invention may be made with a large variety of materials.

A variety of fluorochemical liquids may be used. Suitable fluorochemical liquids include straight and branched chain and cyclic perfluorocarbons, straight and branched chain and cyclic perfluoro tertiary amines, straight and branched chain and cyclic perfluoro ethers and thioethers, chlorofluorocarbons and polymeric perfluoro ethers and the like. Although up to 50% hydrogen-substituted compounds can be used, perhalo compounds are preferred. Most preferred are perfluorinated compounds. Exemplary fluorochemicals useful in the present invention are commercially available materials such as the fluorochemicals sold with the trademarks Kel-F ® and Fluorinerts ® (3M, St. Paul, Minn.), Freon ® and Series E (DUpont, Wilmington, Del.) and Fomblins ® (Montedison, Italy).

Although any fluorochemical liquid i.e. a substance which is a liquid at about 20°C. at atmospheric pressure, can be used to prepare a fluorochemical emulsion of the present invention, for many purposes emulsions with longer extended stability are preferred. In order to obtain such emulsions, fluorochemical liquids with boiling points above 30° C are preferred. Preferably the fluorochemical liquids have boiling points above 50°C., and most preferred are fluorochemical liquids with boiling points above about 100° C.

Suitable fluorochemical liquids include perfluorodecalin, perfluoro-n-pentane, perfluoromorpholine, perfluorotriamylamine, perfluorodimethylcyclohexane, perfluorodicyclohexyl ether, perfluoro-n-butyltetrahydrofuran, perfluoro-n-octyl bromide, perfluorotri-n-butylamine, and compounds which are structurally similar to these compounds and are partially or fully halogenated (including at least some fluorine substituents) or partially or fully perfluorinated.

Emulsifying agents, for example surfactants, may be used to facilitate the formation of emulsions. Typically, aqueous phase surfactants have been used to facilitate the formation of emulsions of fluorochemical liquids. One of the primer materials such as albumiris, polysaccharides, and phospholipids may be used as an emulsifying agent. Other known surfactants such as Pluronic F-68, a block copolymer of $-O(CH_2)_2-O-(CH_2)_2-O-$ and $-O-(CH_2)_3-O-(CH_2)_3-O-$, may be used.

Some examples of suitable surfactants are anionics, such as those sold with the trade names:
Hamposyl TM L30 (W.R. Grace Co., Nashua, N.H.),
Sodium dodecyl sulfate,
Aerosol 413 (American Cyanamid Co., Wayne, N.J.),
Aerosol 200 (American Cyanamid Co.),
Lipoproteol TM LCO (Rhodia Inc., Mammoth, N.J.), Standapol TM SH 135 (Henkel Corp., Teaneck, N.J.),
Fizul TM 10-127 (Finetex Inc., Elmwood Park, N.J.), and
Cyclopol TM SBFA 30 (Cyclo Chemicals Corp., Miami, Fla.);

amphoterics, such as those sold with the trade names:
Deriphat TM 170 (Henkel Corp.),
Lonzaine TM JS (Lonza, Inc.),
Niranol TM C2N-SF (Miranol Chemical Co., Inc., Dayton, N.J.),
Amphoterge TM W2 (Lonza, Inc.), and
Amphoterge TM 2WAS (Lonza, Inc.);

non-ionics, such as those sold with the trade names:
Pluronic TM F-68 (BASF Wyandotte, Wyandotte, Mich.),
Pluronic TM F-127 (BASF Wyandotte),
Brij TM 35 (ICI Americas; Wilmington, Del.),
Triton TM X-100 (Rohm and Haas Co., Philadelphia, Pa.),
Brij TM 52 (ICI Americas),
Span TM 20 (ICI Americas),
Generol TM 122 ES (Henkel Corp.),
Triton TM N-42 (Rohm and Haas Co.,),
Triton TM N-101 (Rohm and Haas Co.,),
Triton TM X-405 (Rohm and tlaas Co.,),
Tween TM 80 (ICI Americas),
Tween TM 85 (ICI Americas), and
Brij TM 56 (ICI Americas).

These surfactants' are used alone or in combination in amounts of 0.10 to 5.0% by weight to assist in stabilizing the emulsions.

Fluorinated surfactants which are soluble in the fluorochemical liquid to be emulsified can also be used. Suitable fluorochemical surfactants include perfluorinated alkanoic acids such as perfluorohexanoic and perfluorooctanoic acids and amidoamine derivatives thereof such as $C_7F_{15}CONH(CH_2)_4N(CH_3)_2$ and 1,1-dihydroperfluoroalcohols such as 1,1-dihydroperfluoro-n-octanol. These surfactants are generally used in amounts of 0.01 to 5.0% by weight, and preferably in amounts of 0.1 to 1.0%.

Other suitable fluorochemical surfactants include perfluorinated alcohol phosphate esters and their salts; perfluorinated sulfonamide alcohol phosphate esters and their salts; perfluorinated alkyl sulfonamide alkylene quaternary ammonium salts; N,N-(carboxyl-substituted lower alkyl) perfluorinated alkyl sulfonamides; and mixtures thereof. As used herein, the term "perfluorinated" means that the surfactant contains at least one perfluorinated alkyl group.

Suitable perfluorinated alcohol phosphate esters include the free acids of the diethanolamine salts of mono- and bis(1H,1H,2H,2H-perfluoroalkyl)phosphates. The phosphate salts, available under the tradename "Zonyl RP" (E.I. Dupont de Nemours and Co., Wilmington, Del.), are converted to the corresponding free acids by known methods. Suitable perfluorinated sulfonamide alcohol phosphate esters are described in U.S. Pat. No. 3,094,547, and have the general formula:

$$[R_fSO_2N(R)R'O]_mP(OH)_{3-m}$$

wherein R is hydrogen or an alkyl group having 1 to about 12 carbon atoms, preferably from 1 to 6 carbon atoms; R' is an alkylene bridging group containing 2 to 12 carbon atoms, preferably from 2 to 8 carbon atoms; $R_f$ is perfluoroaliphatic $C_nF_{2n+1}$ or perfluorocycloaliphatic $C_nF_{2n-1}$ (n is an integer from 1 to 18, preferably from 6 to 12); and m is an integer from 1 to 3. Although each of the mono-, di- and triesters are useful, the diester is most readily available commercially. Suitable perfluorinated sulfonamide alcohol phosphate esters and salts of these include perfluoro-n-octyl-N-ethylsulfonamidoethyl phosphate, bis(perfluoro-n-octyl-N-ethylsulfonamidoethyl) phosphate, the ammonium salt of bis(perfluoro-n-octyl-N-ethylsulfonamidoethyl)phosphate, bis(perfluorodecyl-N-ethylsulfonamidoethyl)-phosphate and bis(perfluorohexyl-N-ethylsulfonamidoethyl)phosphate.

The preferred formulations use Pluronic F-68 as the aqueous surfactant in phosphate buffered saline and perfluoroamidoamines and perfluorodihydroalcohols as the fluorochemical surfactants.

The fluorochemical emulsion can be prepared with or without a primer material. Suitable primer materials include proteins such as albumins (e.g. bovine serum albumin and ovalbumin), casein, whole sera such as normal human serum, fibrinogen, collagens, synthetic poly(amino acids) e.g. poly(lysine-phenylalanine) and polylysine. Primer materials rich in lysine content produce emulsions droplets which are highly active in coupling reactions. Use of copolymers which have a one to one ratio of lysine with a hydrophobic amino acid such as alanins or phenylalanine as primer materials results in a very high concentration of amino groups available for coupling reactions. These lysine-hydrophobic amino acid copolymers are adsorbed tightly with the hydrophobic residues interacting with the fluorochemical fluid phase. In some cases, however, the use of the copolymer alone as a primer material may result in crosslinking of emulsion droplets during coupling reactions with specific binding species. A mixture of bovine serum albumin and copolymer alleviates the crosslinking problem, however the amount of specific binding species that, can be coupled is also reduced. Other suitable primer materials include naturally occurring or synthetic polymers which are highly charged such as charged polysaccharides e.g. heparin, dextran sulfate, DIMA (a dimethylamine adduct of expoxidized polybutadiene as disclosed, in U.S. Pat. No. 4,210,722), protamine sulfate, nucleic acids and the like.

The emulsions of the present invention may be prepared by various techniques. One method is sonication of a mixture of a fluorochemical liquid and an aqueous solution containing a suitable primer material or specific binding species. Generally, these mixtures include a surfactant. Cooling the mixture being emulsified, minimizing the concentration of surfactant, and buffering with a saline buffer will maximize both retention of specific binding properties and the coupling capacity of the primer material. These techniques provide excellent emulsions with high activity per unit of absorbed primer material or specific binding species.

When high concentrations of a primer material or specific binding species coated on fluorochemical droplets are desired, the mixture should be heated during sonication, the mixture should have a relatively low ionic strength, and the aqueous solution should have a moderate to low pH. Too low an ionic strength, too low a pH and too much heat in some cases may cause some degradation or loss of all of the specific binding properties of the specific binding species or the coupling capacity of the primer material. Careful control and variation of the emulsification conditions will optimize the properties of the primer material or the specific binding species while obtaining high concentrations of coating. Variation of ionic strength, pH, and temperature have been found to be particularly valuable where bovine serum albumin is the primer material.

The quality of the emulsions obtained can be evaluated by conventional techniques such as visual observation, nephelometry, coulter counter measurement or spectrophotometric measurement. When suitable indicators are included in the emulsion components, such as dyes or fluorescent and chemiluminescent markers, the emulsion droplets can be observed by the properties of these materials. The useful emulsions may have a wide range of mean droplet diameters, e.g., from as small as 0.01 microns to as large as 500 microns. The droplet sizes can be controlled and varied by modifications of the emulsification techniques and the chemical components.

While preparation of emulsions by sonication has been acceptable, some degree of variability of droplet size distribution of the droplets is observed. An alternative method of making the emulsions involves directing high pressure streams of mixtures containing the aqueous solution, a primer material or the specific binding species, the fluorocarbon liquid and a surfactant (if any) so that they impact one another to produce emulsions of narrow droplet size distribution and small droplet size. The Microfluidizer TM apparatus (Microfluidics, Newton, Mass.) is used to make the preferred emulsions. The apparatus is also useful to process emulsions made by sonication or other conventional methods. Feeding a stream of droplets through the Microfluidizer TM apparatus yields emulsions having narrow droplet size distribution and small droplet size.

The specific binding species may be immobilized on the fluorochemical droplet surface by direct adsorption or by chemical coupling. Examples of specific binding species which can be immobilized by direct adsorption include antibodies, protein A, and enzymes. To make such an emulsion the specific binding species may be suspended or dissolved in the aqueous phase prior to formation of the emulsion. Alternatively, the specific binding species may be added after formation of the emulsion and incubated with agitation at room temperature (25° C.) in a pH 7.0 buffer (typically phosphate buffered saline) for 1.2 to 18 hours.

Where the specific binding species is to be coupled to a primer material, conventional coupling techniques may be used. The specific binding species may be covalently bonded to primer material with coupling agents using methods which are known in the art. One type of coupling agent uses a carbodiimide such as 1-ethyl-3-(3-N,N-dimethylaminopropyl)carbodiimide hydrochloride or 1-cyclohexyl-3-(2-morpholinoethyl)carbodiimide methyl-p-toluenesulfonate. Other suitable coupling agents include aldehyde coupling agents having either ethylenic unsaturation such as acrolein, methacrolein, or 2-butenal, or having a plurality of aldehyde groups such as glutaraldehyde, propanedial or butanedial. Other coupling agents include 2-iminothiolane hydrochloride, bifunctional N-hydroxysuccinimide esters such as disuccinimidyl subsrate, disuccinimidyl tartrate, bis[2-(succinimidooxycarbonyloxy)ethyl]sulfone, disuccinimidyl propionate, ethylene glycolbis(succinimidyl succinate); heterobifunctional reagents such as N-(5-azido-2-nitrobenzoyloxy)succinimide, p-azidophenylbromide, p-azidophenylglyoxal, 4-fluoro-3-nitrophenylazide, N-hydroxysuccinimidyl-4-azidobenzoate, m-maleimidobenzoyl N-hydroxysuccinimide ester, methyl-4-azidophenylglyoxal, 4-fluoro-3-nitrophenyl azide, N-hydroxysuccinimidyl-4-azidobenzoate hydrochloride, p-nitrophenyl 2-diazo-3,3,3-trifluoropropionate, N-succinimidyl-6-(4'-azido-2'-nitrophenylamino)hexanoate, succinimidyl 4-(N-maleimidomethyl)cyclohexane-1-carboxylate, succinimidyl 4-(p-maleimidophenyl)butyrate, N-succinimidyl(4-azidophenyldithio)propionate, N-succinimidyl 3-(2-pyridyldithio)propionate, N-(4-azidophenylthio)phthalamide; homobifunctional reagents such as 1,5-difluoro-2,4-dinitrobenzene, 4,4'-difluoro-3,3'-dinitrodiphenylsulfone, 4,4'-diisothiocyano-2,2'-disulfonic acid stilbene, p-phenylenediisothiocyanate, carbonylbis(L-methionine p-nitrophenyl ester), 4,4'-dithiobisphenylazide, erythritolbiscarbonate and bifunctional imidoesters such as dimethyl adipimidate hydrochloride, dimethyl suberimidate, and dimethyl 3,3'-dithiobispropionimidate hydrochloride. Covalent bonding of a specific binding species to the primer material can be carried out with the above reagents by conventional, well-known reactions, for example, in the aqueous solutions at a neutral pH, at temperatures of less than 25° C. for 1 hour to overnight.

In some applications the emulsions of the present invention are more useful if the fluorochemtcal droplets incorporate dye which can be detected by spectrophotometric, fluorometric, or colorimetric means. For example, agglutination end points are more easily observed with the naked eye when the fluorochemical droplet is colored. Suitable dyes useful for this purpose are dyes sufficiently soluble in fluorinated liquids to color the liquid. The preferred dyes are soluble in perfluorinated liquids. Such dyes will typically possess one or more solubilizing groups such as halogenated side chains or preferably a perfluorinated side chain such as a perfluoroalkyl or perfluoroalkyl ether side chain or perfluorinated cyclic group. Some examples of suitable dyes are the perfluoroalkylated phthalein, phthalocyanine, rhodamine, and quinophthaline dyes described in U.S. Pat. No. 3,281,426 which is hereby incorporated by reference. Representative dyes described in that patent are thioindigo (pink), pyranthrone (orange), violanthrone (dark blue), isoviolanthrone (violet), and Tiers' Blue, a copper phthalocyanine substituted by perfluoroalkyl groups:

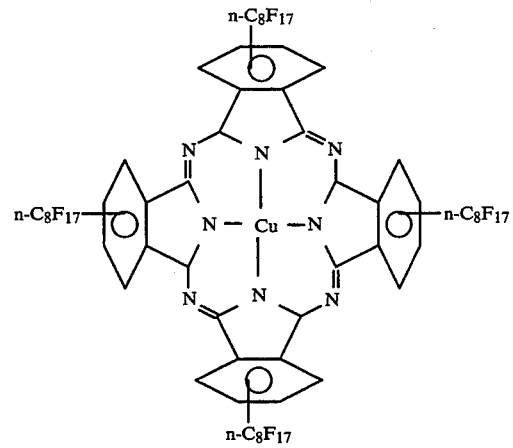

A substituted methyl red analog with a perfluoroalkyl group is:

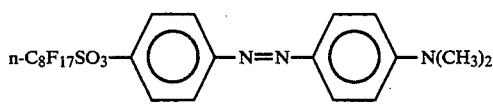

Other suitable dyes are perfluoroalkyl-beta-diketone lanthanide complexes such as,

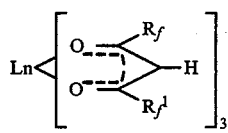

wherein $R_f$ and $R^1_f$ are perfluoroalkyl or perfluoroaryl and the like.

The soluble dyes may be dissolved in the fluorochemical liquid to be emulsified before emulsification by simple mixing, optionally with heating. Alternatively, the addition of the soluble dye and the emulsification may be carried out simultaneously using standard emulsification techniques such as sonication and mechanical emulsification as obtained using a motorized french press, Model FA-078 (available from SLM Instruments, Inc., Urbana, Ill.). Dye can be added to the emulsions after the formation of the emulsions, although this operation may be more difficult because the primer material or the specific binding species may act as a barrier.

Combinations of different dyes in separate droplets offer the possibility of preparing emulsions of any color. Selective removal of one color of droplets due to an antibody-antigen aggregation reaction for example, would cause a change in the apparent color of the emulsion. Also dyed droplets which are adhered to a dipstick, due to an antigen-antibody reaction, would produce a color on a dipstick. Both of these approaches have the potential of producing an easily interpreted, qualitative endpoint for a number of immunoassays.

Dye precursors may also be used. For instance, color forming agents may be associated with the surface of droplets so that they can couple to an appropriate material to form dyes (a type of color coupling technique). This could be accomplished using the diazo salt used to produce the perfluoroalkyl methyl red material described above.

Further aspects of the invention, including the process of using the emulsions, will be apparent from the following non-limiting examples.

EXAMPLE 1

In order to compare the formation of fluorochemicals emulsions in a standard way, each of fluorochemicals fluids shown in Table 1 was emulsified by sonication in an ice bath cooled rosette cell for five minutes. Each fluorochemical liquid (100 microliters) was dispersed at a concentration of 1 volume % in 10 ml of aqueous saline, phosphate buffered to pH 7 and containing 0.5% by weight Plutonit F-68 as a surfactant.

These solutions were evaluated after one day and again after 7 days for droplet size by recording the amount of sedimentation. Droplet size was determined on a qualitative basis under 400×magnification with dark field illumination after 1 and 7 days.

The low boiling perfluorocarbons FC-78 and FC-88 and the chlorofluorocarbons Freon 113 and Kel-F1 formed poorer quality emulsions than the rest of the substances. The presence of nitrogen or oxygen in the fluorinated compounds appeared to result in increased emulsion stability and decreased droplet size in this group of substances.

TABLE 1

| | PERFLUORINATED LIQUID |
|---|---|
| 1. | Decalin (PP-5: DuPont) |
| 2. | n-Pentane (FC-88: 3M) |
| 3. | Morpholine (FC-78: 3M) |
| 4. | Tri-n-amylamine (FC-70: 3M) |
| 5. | Dimethylcyclohexane (FC-82: 3M) |
| 6. | Polyether E-2 (DuPont) |
| 7. | Polyether E-5 (DuPont) |
| 8. | Kel F-1 (3M) (Cl—(CF$_2$—CClF)$_2$—Cl) |
| 9. | Fomblin LS (Montedison) $(-OCF-CF_2)_m-O-(CF_2-O)_mCl$ with $CF_3$ |
| 10. | Freon 113 (DuPont) (Cl$_3$CCF$_3$) |
| 11. | Dicyclohexyl ether (DCE) |
| 12. | Octyl Bromide (OB) |
| 13. | Tri-n-butylamine (FC-43: 3M) |
| 14. | C-8 Cyclic ether (FC-75: 3M) |
| 15. | C-8 Mixture (FC-77: 3M) |

EXAMPLE 2

A fluorochemical cosurfactant consisting of perfluoro-n-octanoic acid or perfluoroamidoamine, $C_7F_{15}C(O)NH(CH_2)_4N(CH_3)_2$ was dissolved in each of the fluorochemical fluids of Table I before the emulsion was prepared as in Example 1. The perfluoroacid-containing fluorochemicals were emulsified in the surfactant buffer described in Example 1 with 0.05 to 0.1% bovine serum albumin (BSA) solution and the perfluoroamidoamine-containing fluorochemicals were emulsified in a 0.05% DIMA solution. These emulsions were also evaluated for droplet size and sedimentation as described in Example 1. Each of the fluorochemicals listed in Table 1 was successfully dispersed as an emulsion with these fluorocarbon and polymer cosurfactants. These emulsions appeared to be more stable and their droplet size was generally smaller than the emulsions prepared without the cosurfactants in Example 1.

EXAMPLE 3

The emulsions prepared in Example 2 were analyzed for the amount of fluorochemical dispersed, the amount of BSA or DIMA bound to the surface of the droplets, and the sizes of the droplets produced. Prior to this analysis the emulsions were separated from free protein by addition of a saturated solution of ammonium sulfate, volume:volume, centrifugation of the precipitate and resuspension of the precipitate in fresh buffer-surfactant solution. This was followed by centrifugation at 30,000×g for 15 minutes and resuspension in fresh buffer-surfactant solution two additional times.

The fluorochemical content of these emulsions was determined by 9as chromatographlc analysts on an OV-101 packed column, 6 feet×0.125 inch. The fluorochemical content was determined by comparison with a standard curve prepared by injection of known amounts of FC-43. Since the response of the flame ionization detector (FID) varied somewhat to the various fluorochemicals emulsified, the fluorochemical content calculated also varied accordingly.

(nitrogen or oxygen). Also, more BSA is bound than is DIMA for all formulations.

The size data indicates emulsions formulated with BSA showed a tendency to aggregate into clumps of droplets while the DIMA emulsions did not. Additionally, the change in numerical score of some of the emulsions over the 7 day period indicates that these preparations are dynamically approaching a more stable size distribution for the particular formulation.

TABLE 2

Fluorocarbon Emulsions Prepared for Quantitative Comparison

| Fluoro-carbon | Emulsifier | Micro Exam 1 day | 7 day | Protein Content mg | Fluoro-carbon Content % |
|---|---|---|---|---|---|
| PP-5 | BSA-Acid | 1.58 | 1.58 | 7.53 | 2.97 |
| | DIMA-Amidoamine | 1.58 | 1.67 | 5.93 | 2.74 |
| FC-70 | BSA-Acid | 1.88 | Agg | 9.95 | 0.71 |
| | DIMA-Amidoamine | 1.88 | 1.59 | 4.74 | 0.68 |
| FC-82 | BSA-Acid | 1.54 | 1.43 | 9.86 | 1.07 |
| | DIMA-Amidoamine | 1.54 | 1.59 | 4.74 | 0.96 |
| E-2 | BSA-Acid | 1.65 | 1.82 | 19.0 | 0.53 |
| | DIMA-Amidoamine | 1.65 | 1.50 | 8.85 | 0.67 |
| E-5 | BSA-Acid | 2.06 | Agg | 13.1 | 0.48 |
| | DIMA-Amidoamine | 2.06 | 2.19 | 5.73 | 0.52 |
| LS | BSA-Acid | 1.65 | Agg | 10.8 | 0.51 |
| | DIMA-Amidoamine | 1.65 | 2.10 | 4.71 | 0.52 |
| DCE | BSA-Acid | Agg | Agg | 14.0 | 0.66 |
| | DIMA-Amidoamine | 1.60 | 2.10 | 7.44 | 0.65 |
| OB | BSA-Acid | 1.60 | 2.03 | 10.1 | 0.54 |
| | DIMA-Amidoamine | 1.60 | 2.59 | 2.66 | 0.25 |
| FC-43 | BSA-Acid | Agg | Agg | 11.3 | 0.59 |
| | DIMA-Amidoamine | 2.03 | 2.54 | 6.04 | 0.62 |
| FC-75 | BSA-Acid | 1.54 | 1.80 | 12.5 | 1.04 |
| | DIMA-Amidoamine | 1.80 | 1.54 | 7.28 | 0.71 |
| FC-77 | BSA-Acid | 2.06 | 1.54 | 12.1 | 0.86 |
| | DIMA-Amidoamine | 2.06 | 1.52 | 9.83 | 0.71 |

Agg = Aggregated droplets.

The amount of BSA and DIMA on the surface of the emulsion droplets was determined by the Bradford method using Coomassie Blue G-250 and a standard curve prepared with known amounts of BSA and DIMA.

The size of emulsion droplets was examined by microscopic evaluation (400×under dark field illumination) and assigned a numerical score on days one and seven after preparation. A numerical score was determined by assigning a value of 1, 2, 3, 4, 5, or 6 to emulsion droplets judged to be about the size of 200, 330, 460, 800, 1200, or above 2500 nanometers, respectively, by comparison to sized polystyrene latex beads (Sigma Chemical). Using a representative microscopic field of each sample, the number of droplets of a particular size range were multiplied by their size value.. The final score for an emulsion was the sum of these size scores divided by the total number of droplets. When an emulsion sample appeared to have a substantial number of droplets aggregated into clumps, the emulsions were noted as aggregated and were not scored further.

The analytical results and scores assigned by microscopic examination of these emulsions are shown in Table 2. This data shows that significant amounts of BSA or DIMA are present on the droplet surface after emulsification and that it is not removed by repeated washing with fresh buffer-surfactant. The amount of BSA or DIMA found bound to the fluorochemical (milligrams per milliliter of fluorochemical emulsion) is greatest in dispersions of FC-43, FC-75, E-2, E-5, and DCE, which are fluorochemicals with heteroatoms

EXAMPLE 4

Emulsions were prepared with a variety of aqueous surfactants by sonication of mixtures containing 1 volume % of FC-43 containing 0.5 weight % of either perfluoroctanoic acid or perfluoroamidoamine, as in example 2, and phosphate buffered saline containing a 0.5 weight % of Emerst 2400, Triton X-100, Tween 40, Pluronic P-85, Pluronic F-38 (nonionic surfactants), lauric acid, Triton X-200, Emersol 6434 (anionic surfactants), Miranol $C_2$M-SF (an amphoteric surfactant), or $C_{10}F_{21}S(O)_2NH-(CH_2)_3-N(CH_3)_3Cl$ (a cationic fluorochemical surfactant) at pH 6.5 to 8.5. Before sonication BSA (0.5% final concentration) was added to perfluoroacid mixtures and DIMA (0.5% final concentration) was added to perfluorooamidoamine mixtures.

The emulsions were evaluated at days 1, 4, and 7 after preparation with regard to sedimentation and emulsion droplet size as noted in Examples 1, 2, and 3 above. Those prepared with nonionic and amphoteric aqueous surfactants were superior to those prepared with anionic or cationic surfactants.

EXAMPLE 5

Emulsions were prepared with 10 volume % FC-43 containing 0.5 to 1.0 weight % $C_7F_{15}CO_2H$ in phosphate buffered saline at pH 7 with either 0.05 weight % Tween 20 or 0.1 weight % $C_7F_{15}CO_2H$ as a surfactant. The resultant emulsions were washed using the centrifugation and resuspension procedure described in Example 3. To a 0.5 milliliter aliquot of these emulsions alkaline phosphatase (Sigma type VIIT) or Protein A (Sigma Chemical Company) were added and incubated for 0.5 to 18 hours. The emulsions were then again washed by the procedure above before being assayed for alkaline phosphatase activity with a chromogenic substrate, p-nitrophenylphosphate, or for protein A activity by agglutination with immunoglublin G (IgG). These assays were positive for the respective specific binding species demonstrating that such materials can be adsorbed to the emulsion droplet and maintain their activity.

EXAMPLE 6

Emulsions were prepared as in Example 4 with the addition of 0.5 weight % of a perfluoroether polymer with terminal ester functional groups $CH_3O_2CC$-$F_2O$—$(CF_2CF_2O)_7(CF_2O)_{14}$—$CF_2CO_2CH_3$ (the $CF_2O$ and $CF_2CF_2O$ units are randomly interspersed) in the FC-43 in place of the perfluoroacid. Alkaline phosphatase was added as in Example 5 and also was found to adsorb to the emulsion droplets.

EXAMPLE 7

Emulsions were prepared with 1 to 5 volume % of FC-43 containing 0.1 to 0.5 weight % each of $C_7F_{15}C(O)NH$—$(CH_2)_4$—$N(CH_3)_3$ and $C_7F_{15}CH_2OH$ in solutions of a series of proteins, synthetic polyamino acids, and polysaccharides as listed in Table 3. The emulsions were prepared by sonication of the FC-43 mixture, addition of an equal volume of phosphate-buffered saline containing 2% by weight Pluronic F-68 at pH 7 and thrice washed by centrifugation at 30,000 g for 15 minutes and by resuspension in fresh surfactant-buffer solution containing no BSA.

The resulting emulsions were coupled to alkaline phosphatase (Sigma Type VIIT) using either Method A, C, E or F, listed below. With each material alkaline phosphatase activity was recovered on the emulsion droplets demonstrating both that the material was adsorbed to the droplet surface and that it was available for immobilization of enzyme antibodies or antigens. The materials thus prepared are suitable for one to detect the presence, concentration, or both of an antigen or antibody in a sample. Emulsions prepared with fibrinogen and ovalbumin tended to aggregate during the processing operations while the other materials produced more acceptable emulsions.

TABLE 3

MATERIALS USED TO PREPARE FLUOROCHEMICAL EMULSION-BIOMOLECULE COMBINATIONS

| Biomolecule in Aqueous Solution | Concentration (mg/ml) | pH |
|---|---|---|
| Bovine Serum Albumin | 0.5 to 10 | 7 or 0 |
| Casein | 2 to 10 | 12 |
| Gelatin | 2 to 10 | 1 |
| Collagen | 1.8 to 3.6 | 3 |
| Ovalbumin | 2 to 5 | 1 |
| Normal Human Serum | 2 to 10 | 5 |
| Fibrinogen | 1 | 11 |
| Protamine Sulfate | 0.5 to 2.0 | 4 or 0 |
| Poly(lysine) | 0.5 to 1.0 | 4 or 0 |
| Poly(phenylalanine-lysine) | 0.5 | 4 or 0 |
| Poly(alanine-lysine) | 0.5 | 4 or 0 |
| Heparin | 1.0 | — |
| Dextran Sulfate | 1.0 | 4 |

EXAMPLE 8

An emulsion was prepared as in Example 7 with BSA in the aqueous phase and washed as in Example 7. To an aliquot of this emulsion the antibody, anti-BSA, was added and upon mixing aggregation of the emulsion occurred which was observed by changes (increases) in the optical density of the emulsion. Using this technique the presence of the antibody was detected and measured semi-quantitatively, using standard curves generated on a spectrophotometer. This result verified that BSA was very tightly bound to the emulsion droplet surface and was antigenically active.

EXAMPLE 9

An aliquot of the emulsion prepared and washed in Example 8 was mixed with fluorescein-labeled anti-BSA producing aggregation of emulsion droplets. These clumps were fluorescent as viewed by a fluorescence microscope indicating that the antibody was acting to crosslink and aggregate the emulsion droplets. This result also verified that BSA is very tightly bound to the droplet surface and. was antigenlcally active.

EXAMPLE 10

Emulsions with 1 volume % FC-43 containing 0.1 weight % each $C_7F_{15}CH_2OH$ and $C_7F_{15}C(O)N$-$H$—$(CH_2)_4N(CH_3)_2$ or $C_7F_{15}C(O)NH$—$C_6H_4N(CH_3)_2$ were prepared in 0.5 weight % poly(phenylalanine-lysine) solution at pH 0 by sonication for 5 minutes in a rosette cell. After sonication the emulsions were stabilized with an equal volume of phosphate buffered saline containing 2.0 weight % Pluronic F-68 and 0.2 weight % triethanolamine. The dispersions were washed by the procedure of Example 7 before being coupled to specific binding species by one of the methods described below.

Substances which have been coupled to emulsions successfully and the methods which have been used for these reactions are shown in Table 4. The substances were coupled alone or in combinations which resulted in separate specific binding activities being recovered intact on the same emulsion droplets. The materials were obtained from commercial sources as follows: Glucose Oxidase (Sigma Type V), horseradish peroxidase (Sigma Type VI), alkaline phosphatase (Sigma Type VIIT), beta-galactosidase (Sigma Grade VIII), wheat germ agglutinin (Triticum vulgaris lectin, Sigma), PHA (Phaseolus vulgaris lectin, Sigma), Protein A (Sigma), rabbit anti-goat IgG (Cappel Laboratories and American Qualex), mouse anti-hCG (Hybritech, Monoclonal), rabbit anti-HRP (Sigma), Goat IgG (Cappel Laboratories), hCG (Sigma), luminol (Sigma), and DL-thyroxin (Sigma).

The coupled emulsions were evaluated for the material immobilized by known procedures, e.g., enzymes by the assay procedures supplied by the source, antibodies with their antigens in agglutination reactions, lectins by red blood cell agglutination, protein A by binding of IgG's and their reaction with antigen and luminol by reaction with peroxide and peroxidase. When combinations of materials were coupled to emulsions, separate assays for each component were carried out.

TABLE 4

Materials Coupled to Fluorochemical Emulsions

| Material | Method |
|---|---|
| Glucose Oxidase | A,C,E,F |
| Horseradish Peroxidase | E,F,I |
| Alkaline Phosphatase | A,B,C,D,G,H |
| Beta-Galactosidase | A |
| Wheat Germ Agglutinin | A |

TABLE 4-continued

Materials Coupled to Fluorochemical Emulsions

| Material | Method |
|---|---|
| Phaseolus vulgaris lectin (PHA) | A |
| anti-Horseradish Peroxidase | A |
| Goat Immunoglobulin G (IgG) | C,E,G |
| anti-Goat IgG | A,G |
| Thyroxin (T-4) | D |
| Luminol | D |
| Human Chorionic Gonadotropin (hCG) | C,G,I |
| anti-hCG | C,G |
| Protein A | A |

METHOD A

Carbodiimide Method 1

To 2 ml of an emulsion (1 to 2% by volume) at pH 7.0 in phosphate buffered saline containing 2% Pluronic F-68 and 0.2% triethanolamine, 0.05 to 1.0 mg of the substance to be coupled was added in water solution (0.1 to mg per ml) followed by 100 to 500 microliters of a carbodiimide reagent (generally 1-[3-(N,N-dimethylamino)propyl]-3-ethylcarbodiimide at 2 mg/ml in water). The mixture was mixed at room temperature for 1 to 2 hours and 0.5 ml each of 1.0M glycine and 10% ethanolamine were added and mixed for an additional two hours. The coupled emulsion was centrifuged at 12,900 g for 30 minutes. The supernatant was discarded and the emulsion pellet resuspended in fresh surfactant buffer. This centrifugation and resuspension procedure was repeated two more times. The resulting emulsion was then ready for use.

METHOD B

Carbodiimide Method 2

The substance to be coupled to the emulsion was activated with carbodiimide reagent solution (as in Method A) at room temperature for 30 to 60 minutes. The ratio of carboiimide reagent was generally in a two to five-fold molar excess. Dialysis for 2 to 6 hours at room temperature with 3 buffer changes or diafiltration with 10 volumes of filtrate was usually satisfactory to remove excess reagent. This activated solution was then added to 2 ml of emulsion and the mixture rotated for 2 to 6 hours at room temperature. As in Method A glycine and ethanolamine were then added to cap activated groups and the coupled emulsion was isolated as described in Method A.

METHOD C

Glutaraldehyde Method 1

To two ml of an emulsion in saline, phosphate-buffered at pH 7.0 containing 2% Pluronic F-68 and 0.2% triethanolamine, the substance to be coupled to the emulsion, 0.05 to 1.0 mg, was added in aqueous solution (0.1 to 10 mg per ml) along with 100 to 500 microliters of 1% glutaraldehyde monomer solution (Sigma Chemical Co., Grade I). The mixture was then mixed at room temperature for 30 to 60 minutes. The reaction was stopped by adding 500 microliters of 10% ethanolamine and mixed for 2 to 18 hours. Sodium borohydride, 500 microliters of 2 mg/ml in water (freshly prepared), was then added and the mixture; rotated for an additional 30 minutes. Clean-up by centrifugation and resuspension was carried out as specified in Method A.

METHOD D

Glutaraldehyde Method 2

The surface of 2 ml of an emulsion in surfactant buffer was activated by reaction with 250 microliters of 1% glutaraldehyde monomer solution for 30 minutes and then dialyzed against surfactant buffer at 4° C. for 18 hours with 3 changes of buffer. Then an aqueous solution of the material to be coupled to the emulsion was added (0.05 to 1.0 mg) and rotated for 18 hours. The coupling reaction was stopped by addition of 500 microliters of 10% ethanolamine and the emulsion recovered by the procedure described in Method A.

METHOD E

Periodate Method 1

A solution of the substance to be coupled was dissolved in 0.3M sodium bicarbonate at about 5 mg/ml, pH 8.1, and was activated by reaction with one milliliter of 0.6M sodium periodate solution for 5 minutes, followed by the addition of one milliliter of 0.16M ethylene glycol solution for 30 minutes. The reaction mixture was then extensively dialyzed against 0.01M sodium bicarbonate. The activated material, 100 to 200 microliters, was then added to two milliliters of emulsion; 100 microliters of sodium cyanoborohydride (100 mg/ml) was added and the mixture rotated for two hours unreacted activated groups were then capped by reaction with 100 microliters of 10% ethanolamine for 1 hour followed by reaction with 1 mg of sodium borohydride for another 30 minutes. The coupled emulsion was then recovered by the centrifugation and resuspension procedures described in Method A.

METHOD F

Periodate Method 2

To 2 ml of emulsion in surfactant buffer and 0.05 to 1.0 mg of the substance to be coupled, 200 microliters of 0.06M sodium periodate at pH 7 and 100 microliters of sodium cyanoborohydride (100 mg/ml) was added and the mixture was rotated for 1 hour. The excess reagent was reacted with 200 microliters of 0.16M ethylene glycol and 200 microliters of 10% ethanolamine for an hour and the coupled emulsion was purified by the centrifugation and resuspension procedure of Method A.

EXAMPLE G

Bifunctional Acid Method 1

To a mixture of 2 ml of emulsion in surfactant buffer and 0.05 to 1.0 mg of substance to be coupled to the emulsion was added 100 microliters of freshly prepared bis(N-hydroxysuccinimidyl)terephthalate solution (10 mg/ml) in N,N-dimethylformamide and the mixture was rotated for 18 hours. Any remaining reagent was then reacted with 500 ul of 1M glycine and 500 ul of 10% ethanolamine for 2 hours. The coupled emulsion was then isolated by centrifugation and resuspension in fresh buffer as in Method A.

METHOD H

Bifunctional Acid Method 2

To a mixture of 2 ml of emulsion in surfactant buffer, was added 0.05 to 1.0 mg of substance to be coupled to the emulsion, and a 100 microliter aliquot of a mixture of 10 mg of a difunctional organic acid which cannot cyclize, such as fumaric or terephthalic acid and 100 microliters of carbonyl diimidizole solution (10 mg/ml) in N,N-dimethylformamide which had reacted for 15 minutes, and the mixture was rotated for 2 hours. Excess reagent was reacted with 500 microliters each of 1M glycine and 10% ethanolamine for 2 hours. The coupled emulsion was then isolated by centrifugation and resuspension in fresh buffer as in Method A.

METHOD I

Cyanate Method

To a mixture of 2 ml of emulsion in surfactant buffer and 0.05 to 1.0 mg of material to coupled to the emulsion was added 100 microliters of a p-nitrophenylcyanate solution (10 mg/ml) in N,N-dimethylformamide, and the reaction mixture was rotated for 30 minutes at room temperature. As the reaction proceeded a yellow color developed from the p-nitrophenol produced from the reaction. Then the mixture was cleaned up by the centrifugation and resuspension procedure of Method A.

EXAMPLE 11

An emulsion was prepared as in Example 7 and was coupled to a mixture of glucose oxidase and horseradish peroxidase by Method E (the Periodate Method I), above. The resulting emulsion, when exposed to glucose and substrate for peroxidase, produced color in proportion to the amount of glucose present. Using o-dianisidine (0.0021M) in 0.05M sodium acetate buffer at pH 5.1 and reference glucose solutions containing from 50 to 500 mg per dl emulsion, the linear reference curve of absorbance at 500 nanometers vs. glucose concentration was plotted indicating that the emulsion may be used to assay for glucose concentration.

EXAMPLE 12

A solution of 0.2% by weight of Tiers' Blue, a perfluoroalkylated copper phthalocyanine dye, in FC-43 was used to prepare emulsions of 1 to 10% by volume of perfluorotri-n-butylamine in phosphate-buffered saline containing 0.5% by weight Pluronic F-68 and 2 mg/ml BSA. The dispersions were effected by sonication for 5 to 10 minutes in an ice-cooled rosette cell. The emulsions were then washed by centrifugation at 30,000 g and resuspended in fresh buffersurfactant solution without BSA thrice. The resulting preparations were highly colored with a slight shift in the absorbance maximum from 610 to 612 nanometers as measured by a Beckman spectrophotometer Model 35.

EXAMPLE 13

A solution of $C_8F_{17}SO_3$—$C_6H_4N$—$NC_6H_4N(CH_3)_2$ in perfluorotri-n-butylamine was used to prepare emulsions of 1 to 10% by volume of perfluorotri-n-butylamine in phosphate buffered saline containing 0.5% by weight Pluronic F-68 and 2 mg/ml BSA. The dispersions were effected by sonication for 5 to 10 minutes in an ice-cooled rosette cell. The emulsions were then washed by centrifugation at 30,000 g and resuspended in fresh buffered surfactant solution without BSA thrice. The washed emulsions were yellow in color, but changed to a red when the solution pH was changed to the range of 2 to 4. The color was associated only with the emulsion droplets, as was shown by centrifuging the emulsion at 30,000 g to completely remove the color from the supernatant.

Portions of the above red emulsions were combined in portions varying from 1 to 1 to 1 to 5 (by volume) of the blue emulsions from Example 12 to form several shades of purple emulsions. The combined emulsions could be changed in color from purple to green by changing the pH of the aqueous solutions.

EXAMPLE 14

Two milligrams of mouse immunoglobin (Ig) (commercially available from Cappel Laboratories, Cochranville, Pa.) was dissolved in 0.15M aqueous sodium chloride solution, and glutaraldehyde was added to provide a weight percent of 1.15%. After two hours at room temperature the activated Ig was chromatographed on Bio-Gel P-2 (commercially available from BioRad Laboratories, Richmond, Calif.) to remove excess glutaraldehyde. One milligram of the activated Ig was combined with 1 ml of a BSA emulsion from Example 7 in phosphate buffered saline of pH 9.0. After the mixture had settled for 24 hours the emulsion was washed to remove unbound Ig and the emulsion tested for immunoreactivity to anti-bovine serum albumin and anti-mouse immunoglobin by capillary immunodiffusion as described in "Handbook of Experimental Immunology", D. M. Weir, ed., Vol. 1 pp. 19.1–19.5, Blackwell Scientific Publications (1973). The results of the evaluation are shown in Table 5. When a solution of antibody is mixed with its corresponding antiserum, the antigen combines with the antibody, and if conditions are suitable, the reactants form precipitating or flocculating aggregates which are readily visible to the naked eye.

TABLE 5

| Antibody Used | Surfactant Only | Fluorochemical Emulsion without Bovine Serum Albumin | Fluorochemical Emulsion with Bovine Serum Albumin | Fluorochemical Emulsion with Bovine Serum Albumin and Immunoglobin |
|---|---|---|---|---|
| Anti-bovine serum albumin | − | − | + | + |
| Anti-immunoblogin | − | − | − | + |

EXAMPLE 15

A sample of the fluorochemical emulsion from Example 7 was conjugated using the method of Example 14 with Streptococcus A-carbohydrate prepared by the method described in Stanford Medical Bulletin 13, 290–291. The ability of free Streptococcus A organisms to inhibit the aggregation of the fluorochemical emulsion-bound Streptococcus A-carbohydrate mixture in the presence of an IgM monoclonal antibody was tested. A combination of the fluorochemical emulsion-bound Streptococcus A-carbohydrate, the antibody and varying concentrations of free Streptococcus A organisms was incubated for 30 minutes at about 20° C. and observed for aggregation. Aggregation was scored on a scale of zero to 4+, with zero being no inhibition of droplet aggregation and 4+ complete inhibition of droplet aggregation. The results are shown in Table 6. They indicate that this method is able to detect organisms at a level of $10^5$ per milliliter.

TABLE 6

| Run Number | Concentration of Organisms (organisms/ml) | Aggregation Inhibition Score |
|---|---|---|
| 1 | $10^8$ | 4+ |
| 2 | $10^7$ | 4+ |
| 3 | $10^6$ | 3+ |
| 4 | $5 \times 10^5$ | 3+ |
| 5 | $10^5$ | 1+ |
| 6 | $5 \times 10^4$ | 0 |
| 7 | $10^4$ | 0 |
| 8 | $10^3$ | 0 |

I claim:

1. A method to bind a first member of a two member specific binding pair contained in an aqueous solution to a second member of the Specific binding pair which is immobilized on an accessible surface of a liquid fluorochemical droplet comprising the steps of
   i) forming a stable fluorochemical emulsion having an aqueous phase and a discontinuous liquid fluorochemical phase by mixing a perfluorinated liquid and a fluorinated surfactant in a buffered aqueous solution containing a water-soluble nonionic or amphoteric surfactant to give a liquid fluorochemical droplet, wherein the fluorochemical droplet consists essentially of a perfluorinated liquid and 0.01–5.0 wt. % of a fluorinated surfactant and wherein the fluorochemical droplet is substantially stable to centrifugation at 30,000×g for fifteen minutes, wherein the perfluorinated liquid is selected from the group consisting of straight chain, branched chain and cyclic perfluorocarbons, straight chain, branched chain and cyclic perfluoro-tertiary amines and straight chain, branched chain and cyclic perfluoroethers and wherein the fluorinated surfactant is selected from the group consisting of perfluorinated alkanoic acids, perfluorinated amidoamines, 1,1-dihydroperfluoroalcohols, and perfluoroether polymers with terminal ester functional groups;
   ii) contacting the liquid fluorochemical droplet with the second member of the specific binding pair, wherein the second member of the specific binding pair is immobilized on the liquid fluorochemical droplet at the continuous-discontinuous interface without a significant loss of activity to give an activated fluorochemical droplet;
   iii) contacting the activated fluorochemical droplet with an aqueous solution containing the first member of the specific binding pair; and
   iv) binding the first member to the second member of the specific binding pair on the fluorochemical droplet.

2. The method of claim 1 wherein the liquid fluorochemical droplet consists of a perfluorinated liquid and 0.1–1.0 wt. % of a fluorinated surfactant.

3. The method of claim 1 wherein the fluorinated surfactant is selected from the group consisting of perfluorohexanoic acid, perfluoroctanoic acid, 1,1-dihydroperfluoro-n-octanol, $CH_3O_2CCF_2O-(CF_2CF_2O)-_7-(CF_2O)_{14}-CF_2CO_2CH_3$ and $C_7F_{15}CONH(CH_2)_4N(CH_3)_2$.

4. The method of claim 1 wherein the first member of the specific binding pair is an antibody and wherein the second member of the specific binding pair is an antigen selected from the group consisting of natural and synthetic proteins, polysaccharides, and nucleic acids.

5. The method of claim 1 wherein the first member of the specific binding pair is an antigen selected from the group consisting of natural and synthetic proteins, polysaccharides, and nucleic acids and the second member of the specific binding pair is an antibody.

6. A method to bind a first member of a two member specific binding pair contained in an aqueous solution to a second member of the specific binding pair which is immobilized on an accessible surface of a liquid fluorochemical droplet comprising the steps of
   i) forming a stable fluorochemical emulsion having an aqueous phase and a discontinuous liquid fluorochemical phase by mixing a perfluorinated liquid and a fluorinated surfactant in a buffered aqueous solution containing a water-soluble nonionic or amphoteric surfactant to give a liquid fluorochemical droplet, wherein the fluorochemical droplet consists essentially of a perfluorinated liquid and 0.01–5.0 wt. % of a fluorinated surfactant and wherein the fluorochemical droplet is substantially stable to centrifugation at 30,000×g for fifteen minutes, wherein the perfluorinated liquid is selected from the group, consisting of straight chain, branched chain and cyclic perfluorocarbons, straight chain, branched chain and cyclic perfluoro-tertiary amines and straight chain, branched chain and cyclic perfluoroethers and wherein the fluorinated surfactant is selected from the group consisting of perfluorinated alkanoic acids, perfluorinated amidoamines, 1,1-dihydroperfluoroalcohols, perfluoroether polymers with terminal ester functional groups;
   ii) contacting the liquid fluorochemical droplet with a primer material selected from the group consisting of proteins, sera, fibrinogen, collagen, polylysinephenylalanine and polylysine to give a primed liquid fluorochemical droplet;
   iii) contacting the primed liquid fluorochemical droplet with a second member of a specific binding pair, wherein the second member of the specific binding pair is immobilized on the primed liquid fluorochemical droplet at the continuous-discontinuous interface without a significant loss of activity to give an activated fluorochemical droplet,
   iv) contacting the activated fluorochemical droplet with an aqueous solution containing the first member of the specific binding pair; and
   v) binding the first member to the second member of the specific binding pair on the fluorochemical droplet.

7. The method of claim 6 wherein the liquid fluorochemical droplet consists of a perfluorinated liquid and 0.1–1.0 wt. % of a fluorinated surfactant.

8. The method of claim 6 wherein the fluorinated surfactant is selected from the group consisting of perfluorohexanoic acid, perfluoroctanoic acid, 1,1-dihydroperfluoro-n-octanol, $CH_3O_2CCF_2O-(CF_2CF_2O)-_7-(CF_2O)_{14}-CF_2CO_2CH_3$ and $C_7F_{15}CONH(CH_2)_4N(CH_3)_2$.

9. The method of claim 6 wherein the first member of the specific binding pair is an antibody and wherein the second member of the specific binding pair is an antigen selected from the group consisting of natural and synthetic proteins, polysaccharides, and nucleic acids.

10. The method of claim 6 wherein the first member of the specific binding pair is an antigen selected from the group consisting of natural and synthetic proteins, polysaccharides, and nucleic acids and the second member of the specific binding pair is an antibody.

11. The method of claim 6 further comprising the step of coupling the second member of the specific binding pair to the primer material with a coupling agent.

12. A method to bind a first member of a two member specific binding pair contained in an aqueous solution to a second member of the specific binding pair which is immobilized on an accessible surface of a liquid fluorochemical droplet comprising the steps of
i) forming a stable fluorochemical emulsion having an aqueous phase and a discontinuous fluorochemical phase by mixing a perfluorinated liquid and a fluorinated surfactant in a buffered aqueous solution containing a water-soluble nonionic or amphoteric surfactant to give a liquid fluorochemical droplet, wherein the fluorochemical droplet consists essentially of a perfluorinated liquid and 0.01–5.0 wt. % of a fluorinated surfactant and wherein the fluorochemical droplet is substantially stable to centrifugation at 30,000×g for fifteen minutes, wherein the perfluorinated liquid is selected from the group consisting of straight chain, branched chain and cyclic perfluorocarbons, straight chain, branched chain and cyclic perfluoro-tertiary amines and straight chain, branched chain and cyclic perfluoroethers and wherein the fluorinated surfactant is selected from the group consisting of perfluorinated alkanoic acids, perfluorinated amidoamines, 1,1-dihydroperfluoroalcohols, and perfluoroether polymers with terminal ester functional groups;
ii) contacting the liquid fluorochemical droplet with a primer material selected from the group consisting of proteins, sera, fibrinogen, collagen, polylysine-phenylalanine and polylysine to give a primed liquid fluorochemical droplet;
iii) contacting the primed liquid fluorochemical droplet with a dye selected from the group consisting of perfluoroalkyl phthalein dye, perfluoroalkyl phthalocyanine dye, perfluoroalkyl rhodamine dye, perfluoroalkyl quinothaline dye and perfluoroalkyl-beta-diketone lanthanide complexes, and with the second member of the specific binding pair, wherein the second member of the specific binding pair is immobilized on the primed fluorochemical droplet at the continuous-discontinuous interface to give an activated fluorochemical droplet;
iv) contacting the activated fluorochemical droplet with an aqueous solution containing the first member of the specific binding pair; and
v) binding the first member to the second member of the specific binding pair on the fluorochemical droplet.

13. The method of claim 12 wherein the liquid fluorochemical droplet consists of of a perfluorinated liquid and about 0.1–1.0 wt. % of a fluorinated surfactant.

14. The method of claim 12 wherein the fluorinated surfactant is selected from the group consisting of perfluorohexanoic acid, perfluoroctanoic acid, 1,1-dihydroperfluoro-n-octanol, $CH_3O_2CCF_2O—(CF_2CF_2O)_7—(CF_2O)_{14}—CF_2CO_2CH_3$ and $C_7F_{15}CONH(CH_2)_4N(CH_3)_2$.

15. The method of claim 12 wherein the first member of the specific binding pair is an antibody and wherein the second member of the specific binding pair is an antigen selected from the group consisting of natural and synthetic proteins, polysaccharides, and nucleic acids.

16. The method of claim 12 wherein the first member of the specific binding pair is an antigen selected from the group consisting of natural and synthetic proteins, polysaccharides, and nucleic acids and the second member of the specific binding pair is an antibody.

17. The method of claim 4 wherein the antigen is a therapeutic substance.

18. The method of claim 5 wherein the antigen is a therapeutic substance.

19. The method of claim 9 wherein the antigen is a therapeutic substance.

20. The method of claim 10 wherein the antigen is a therapeutic substance.

21. The method of claim 15 wherein the antigen is a therapeutic substance.

22. The method of claim 16 wherein the antigen is a therapeutic substance.

23. The method of claim 11 wherein the coupling agent is selected from the group consisting of 1-ethyl-3-(3-N,N-dimethylaminopropyl)carbodiimide hydrochloride, 1-cyclohexyl-3-(2-morpholinoethyl)carbodiimide methyl-p-toluenesulfonate, acrolein, methacrolein, 2-butenal, glutaraldehyde, propanedial, butanedial, 2-iminothiolane hydrochloride, disuccinimidyl suberate, disuccinimidyl tartrate, bis[2-(succinimidooxycarbonyloxy)ethyl]sulfone, disuccinimidyl propionate, ethylene glycolbis(succinimidyl succinate), N-(5-azido-2-nitrobenzoyloxy)succinimide, p-azidophenylbromide, p-azidophenylglyoxal, 4-fluoro-3-nitrophenylazide, N-hydroxysuccinimidyl-4-azidobenzoate, m-maleimidobenzoyl N-hydroxysuccinimide ester, methyl-4-azidophenylglyoxal, 4-fluoro-3-nitrophenyl azide, N-hydroxysuccinimidyl-4-azidobenzoate hydrochloride, p-nitrophenyl 2-diazo-3,3,3-trifluoropropionate, N-succinimidyl-6-(4'-azido-2'-nitrophenylamino)hexanoate, succinimidyl 4-(N-maleimidomethyl)cyclohexane-1-carboxylate, succinimidyl 4-(p-maleimido-phenyl)butyrate, N-succinimidyl(4-azidophenyldithio)-propionate, N-succinimidyl 3-(2-pyridyldithio)propionate, N-(4-azidophenylthio)phthalamide, 1,5-difluoro-2,4-dinitrobenzene, 4,4'-difluoro-3,3'-dinitrodiphenylsulfone, 4,4'-diisothiocyano-2,2'-disulfonic acid stilbene, p-phenylenediisothiocyanate, carbonylbis(L-methionine p-nitrophenyl ester), 4,4'-dithiobisphenylazide, erythritolbiscarbonate, dimethyl adipimidate hydrochloride, dimethyl suberimidate, and dimethyl 3,3'-dithiobispropionimidate hydrochloride.

* * * * *

UNITED STATES PATENT AND TRADEMARK OFFICE
CERTIFICATE OF CORRECTION

PATENT NO. : 5,401,634                                     Page 1 of 2
DATED     : March 28, 1995
INVENTOR(S) : Dean S. Milbrath It is certified that error appears in the above-indentified patent and that said Letters Patent is hereby corrected as shown below:

| | |
|---|---|
| Col. 3, line 27 | "tile" should read --the-- |
| Col. 4, line 56 | "albumiris" should read --albumins-- |
| Col. 5, line 9 | "Niranol™ C2N-SF" should read --Miranol™ C2M-SF-- |
| Col. 5, line 25 | "tlass" should read --Haas-- |
| Col. 6, line 27 | "alanins" should read --alanine-- |
| Col. 7, line 46 | "1.2" should read --12-- |
| Col. 7, line 56 | "aidehyde" should read --aldehyde-- |
| Col. 7, line 58 | "aidehyde" should read --aldehyde-- |
| Col. 7, line 62 | "subsrate" should read --suberate-- |
| Col. 9, line 59 | "Plutonit" should read --Pluronic-- |
| Col. 10, line 63 | after "sulfate," insert --1:1-- |
| Col. 11, line 2 | "9as chromatographlc analysts" should read --gas chromatographic analysis-- |
| Col. 11, line 53 | delete "value.." and insert --value.-- |

UNITED STATES PATENT AND TRADEMARK OFFICE
CERTIFICATE OF CORRECTION

PATENT NO. : 5,401,634
DATED : March 28, 1995
INVENTOR(S) : Dean S. Milbrath

It is certified that error appears in the above-indentified patent and that said Letters Patent is hereby corrected as shown below:

Col. 13, line 16    "$CF_{20}$" should read --$CF_2O$--

Col. 14, line 18    delete "and." and insert --and--; "antigenlcally" should read --antigenically--

Col. 18, line 22    "1.15%" should read --1.25%--

Col. 22, lines 4-5    "$CH_3O_2CCF_2O\text{-}(CF_2CF_{20})_7\text{-}(CF_2O)_{14}\text{-}CF_2CO_2CH_3$" should read -- $CH_3O_2CCF_2O\text{-}(CF_2CF_2O)_7\text{-}(CF_2O)_{14}\text{-}CF_2CO_2CH_3$ --

Signed and Sealed this

Nineteenth Day of September, 1995

Attest:

BRUCE LEHMAN

*Attesting Officer*      *Commissioner of Patents and Trademarks*